US00PP36310P2

(12) United States Plant Patent
van Dijk

(10) Patent No.: US PP36,310 P2
(45) Date of Patent: Dec. 10, 2024

(54) ***ANTHURIUM* PLANT NAMED 'AN2180756'**

(50) Latin Name: *Anthurium andreanum*
Varietal Denomination: AN2180756

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/607,501

(22) Filed: Mar. 17, 2024

(51) Int. Cl.
*A01H 5/02* (2018.01)
*A01H 6/00* (2018.01)

(52) U.S. Cl.
USPC ..... Plt./365

(58) Field of Classification Search
USPC ..... Plt./365, 367
CPC ..... A01H 5/02; A01H 5/00; A01H 6/00
See application file for complete search history.

(56) References Cited

U.S. PATENT DOCUMENTS

PP27,889 P3 * 4/2017 Van Dijk ..... A01H 6/00
Plt./368

OTHER PUBLICATIONS

CPVO Register Version 4.20.1 retrieved on Jul. 9, 2024 at https://online.plantvarieties.eu/publicConsultation Details?registerId=20222633&denomination=an2180756, 2 pp. (Year: 2024).*

UPOV Pluto 20240709 retrieved on Jul. 9, 2024 at https://plluto.upov.int/result, one page (Year: 2024).*

* cited by examiner

*Primary Examiner* — June Hwu
(74) *Attorney, Agent, or Firm* — C. Anne Whealy

(57) ABSTRACT

A new and distinct cultivar of *Anthurium* plant named 'AN2180756', characterized by its upright to outwardly arching and uniform plant habit; freely clumping growth habit; bushy and dense plants; ovate to narrowly ovate to close to narrowly deltoid dark green-colored leaves; freely flowering habit; inflorescences that are positioned within to slightly above the foliar plane on strong and erect scapes; broadly ovate and strongly concave purplish pink and yellowish green-colored spathes and light purplish pink and yellowish green-colored spadices; and durable spathes that impart good inflorescence longevity.

2 Drawing Sheets

Figure 1:
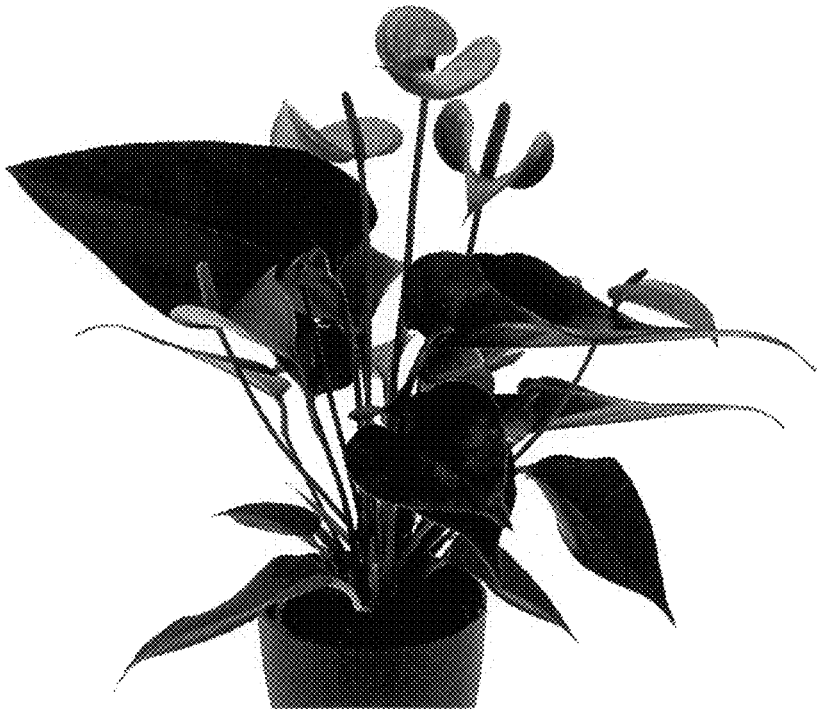

Botanical designation: *Anthurium andreanum*
Cultivar denomination: 'AN2180756'

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Anthura B. V. of Bleiswijk, The Netherlands on Nov. 22, 2022, application number 2022/2633. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Anthurium* plant, botanically known as *Anthurium andreanum* and hereinafter referred to by the name 'AN2180756'.

The new *Anthurium* plant is a product of a controlled breeding program conducted by the Inventor in Bleiswijk, The Netherlands. The objective of the breeding program is to create new vigorous *Anthurium* plants with durable, large and attractive spathes.

The new *Anthurium* plant is a naturally-occurring whole plant mutation of *Anthurium andreanum* 'Anthucoen', disclosed in U.S. Plant Pat. No. 22,630. The new *Anthurium* was discovered and selected by the Inventor as a single flowering plant from within a population of plants of 'Anthucoen' in a controlled greenhouse environment in Bleiswijk, The Netherlands in October 2016.

Asexual reproduction of the new *Anthurium* plant by in vitro meristem propagation in a controlled environment in Bleiswijk, The Netherlands since January 2017 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2180756'. These characteristics in combination distinguish 'AN2180756' as a new and distinct *Anthurium* plant:

1. Upright to outwardly arching and uniform plant habit.
2. Freely clumping growth habit; bushy and dense plants.
3. Ovate to narrowly ovate to close to narrowly deltoid dark green-colored leaves.
4. Freely flowering habit.
5. Inflorescences that are positioned within to slightly above the foliar plane on strong and erect scapes.
6. Broadly ovate and strongly concave purplish pink and yellowish green-colored spathes and light purplish pink and yellowish green-colored spadices.
7. Durable spathes that impart good inflorescence longevity.

Plants of the new *Anthurium* differ primarily from plants of the mutation parent, 'Anthucoen', in spathe color as spathes of plants of the new *Anthurium* are purplish pink and yellowish green in color whereas spathes of plants of 'Anthucoen' are red purple in color. In addition, leaf apices of plants of the new *Anthurium* are apiculate with a mucronate tip whereas leaf apices of plants of 'Anthucoen' are narrowly acute.

Plants of the new *Anthurium* can also be compared to plants of *Anthurium andreanum* 'Anthdubaq', disclosed in U.S. Plant Pat. No. 27,889. In side-by-side comparisons, plants of the new *Anthurium* differ primarily from plants of 'Anthdubaq' in the following characteristics:

1. Spathes of plants of the new *Anthurium* are purplish pink and yellowish green in color whereas spathes of plants of 'Anthdubaq' are red purple in color.
2. Spathes of plants of the new *Anthurium* are strongly concave whereas spathes of plants of plants of 'Anthdubaq' are weakly concave.
3. Spadices of plants of the new *Anthurium* are light purplish pink and yellowish green in color whereas spadices of plants of 'Anthdubaq' are purple in color.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2180756' grown in a container.

Figure 2:
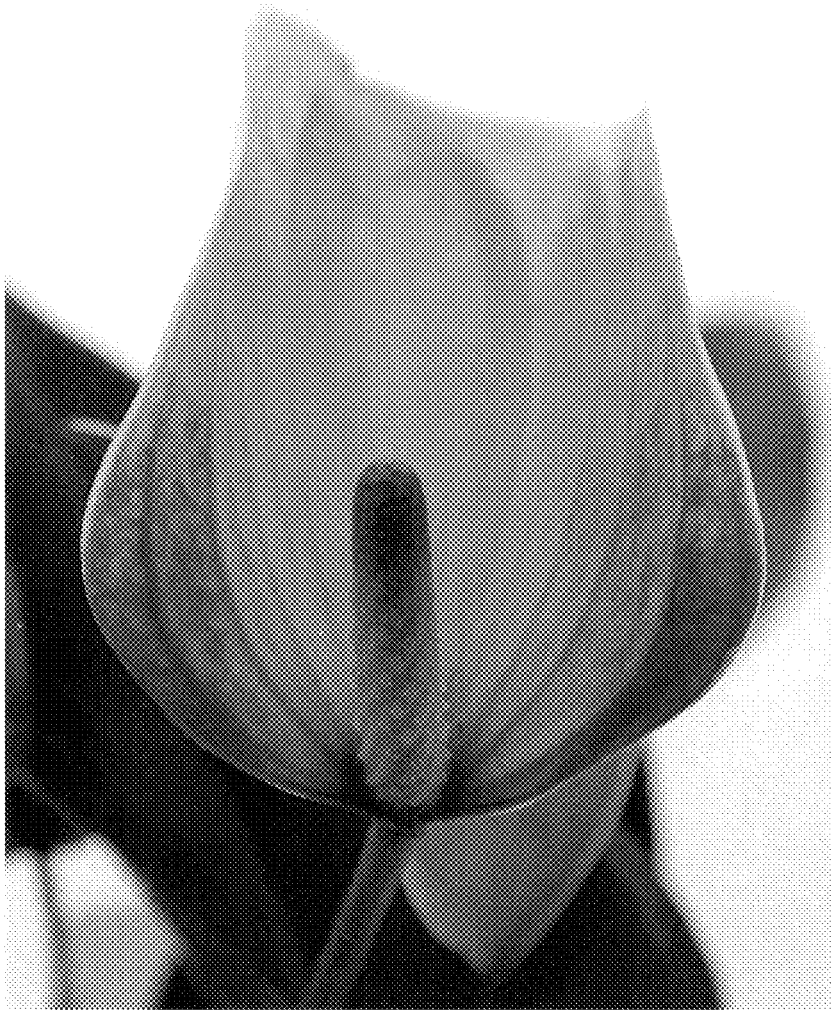

The photograph on the second sheet (FIG. 2) is a close-up view of a typical inflorescence of 'AN2180756'.

DETAILED BOTANICAL DESCRIPTION

The aforementioned photographs and following observations and measurements describe plants grown in 9-cm containers in Bleiswijk, The Netherlands during the summer in a glass-covered greenhouse. Plants were grown under conditions and practices which approximate those generally used in commercial *Anthurium* production. During the production of the plants, day and night temperatures ranged from about 19° C. to 22.5° C. and light levels ranged from 100 μmol to 200 μmol. Plants were nine months old when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2180756'.

Parentage: Naturally-occurring whole plant mutation of *Anthurium andreanum* 'Anthucoen', disclosed in U.S. Plant Pat. No. 22,630.

Propagation:

*Type*.—By in vitro meristem propagation.

*Time to initiate roots, summer and winter*.—About two weeks at temperatures about 19° C. to 22.5° C.

*Time to produce a rooted young plant, summer and winter*.—About six to eight weeks at temperatures about 19° C. to 22.5° C.

*Root description*.—Medium in thickness, fibrous; typically light yellow in color, actual color of the roots is dependent on substrate composition, water quality, fertilizer type and formulation, substrate temperature and physiological age of roots.

*Rooting habit*.—Freely branching, medium density.

Plant description:

*Plant shape*.—Upright to outwardly spreading and uniform plant habit; overall shape, broadly ovate to broadly obovate.

*Growth habit*.—Freely clumping habit with about five clumps per plant imparting a bushy and dense appearance; moderately vigorous growth habit and moderate to slow growth rate.

*Plant height, from soil level to top of leaf plane*.—About 20 cm.

*Plant height, from soil level to top of inflorescences*.—About 24.4 cm.

*Plant diameter or spread*.—About 34.5 cm.

Leaf description:

*Arrangement*.—Alternate; simple; about four leaves per clump.

*Length*.—About 13.8 cm.

*Width*.—About 8.3 cm.

*Shape*.—Ovate to narrowly ovate to close to narrowly deltoid.

*Apex*.—Apiculate with mucronate apex.

*Base*.—Broadly truncate to broadly and shallowly cordate.

*Margin*.—Entire; slightly and coarsely undulate.

*Texture and luster, upper and lower surfaces*.—Smooth, glabrous; moderately leathery; glossy.

*Venation pattern*.—Pinnate.

*Color*.—Developing leaves, upper surface: Slightly darker and more intense than a blend of 143A and 144A. Developing leaves, lower surface: Slightly darker and more intense than 144A. Fully expanded leaves, upper surface: Slightly darker than a blend of 139A and 147A; venation, close to 143A. Fully expanded leaves, lower surface: Close to a blend of 143B and 146B; venation, close to 145A.

*Petioles*.—Length: About 10.7 cm. Diameter: Distally, about 3 mm; proximally, about 4 mm. Strength: Strong. Texture and luster, upper and lower surfaces: Smooth, glabrous; slightly glossy. Color, upper surface: Close to 144A. Color, lower surface: Close to 144A to slightly lighter than 144A. Geniculum length: About 1.7 cm. Geniculum diameter: About 3.5 mm. Geniculum texture and luster, upper and lower surfaces: Smooth, glabrous; slightly glossy. Geniculum color, upper surface: Close to 144A. Geniculum color, lower surface: Close to a blend of 144A and 144B. Wing length: About 1.7 cm. Wing diameter: About 4 mm. Wing color: Close to 144B.

Inflorescence description:

*Inflorescence arrangement and flowering habit.*—Spathes with spadices held within and slightly above the foliar plane on strong and erect scapes; flowering structures arise from leaf axils; freely and continuous flowering year-round in controlled temperature greenhouses in The Netherlands; typically about nine developing and developed inflorescences per plant at one time; inflorescence development commences about 2.5 to 3.5 months after planting.

*Inflorescence longevity*.—Spathes maintain good substance for about two months on the plant; inflorescences persistent.

*Fragrance*.—None detected.

*Spathes*.—Length: About 6.7 cm. Width: About 6.1 cm. Shape: Broadly ovate; strongly concave. Apex: Apiculate. Base: Truncate to broadly and shallowly obtuse. Margin: Entire. Aspect: At about 80° From the peduncle axis. Texture and luster, upper and lower surfaces: Smooth, glabrous; moderately leathery; glossy. Color: When developing, front surface: Close to 76A to 76C; towards the base, tinged with close to 143C and 144C. When developing, rear surface: Close to 76B; towards the base, close to 144C and 144D. Fully developed, front surface: Close to 186C to slightly lighter than 186C with venation, close to N77C; towards the base, close to 144B to 144D with venation, close to NN137A, and at the base, close to N77B; with subsequent development, color becoming closer to 51B and 51C and towards the base, close to 50B, at the margins and base, close to 143A with venation, close to NN137A. Fully developed, rear surface: Close to a blend of 75D and 186D with venation, close to N77C; towards the base, close to 146D and 147D with venation, close to 143A; with subsequent development, color becoming closer to N170D flushed with close to 146C and 146D and towards the margins and base, close to 145A, with venation, close to NN137B.

*Spadices*.—Length: About 3 cm. Diameter: About 7 mm. Shape: Columnar, slightly tapering towards the apex; apex, obtuse; base, obtuse; in cross-section, rounded. Aspect: About 7.5° From the peduncle axis. Color: Immature: Close to 164B; distally, close to 146D. Mature: Close to a blend of 76B and 186D. Flowers: Type: Hermaphroditic. Quantity per spadix: Numerous, about 80. Height: Less than 0.5 mm. Diameter: About 2 mm. Shape: Roughly square. Anther color: Close to 147D. Pollen amount: Scarce. Pollen color: Close to 155A. Stigma color: Close to 186D.

*Scape*.—Length: About 17 cm. Diameter: About 3.5 mm. Strength: Strong. Aspect: About 15° From vertical. Color: Close to 144A.

*Seed and fruit*.—To date, seed and fruit development has not been observed on plants of the new *Anthurium*.

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures about 30° C. and to be hardy to USDA Hardiness Zone 10.

It is claimed:

1. A new and distinct *Anthurium* plant named 'AN2180756' as herein illustrated and described.

* * * * *